United States Patent [19]

Wiley et al.

[11] 4,086,245

[45] Apr. 25, 1978

[54] ANTIBIOTICS 7-O-ALKYLNOGAROLS

[75] Inventors: Paul F. Wiley, Kalamazoo; David J. Houser, Portage, both of Mich.

[73] Assignee: The Upjohn Company, Kalamazoo, Mich.

[21] Appl. No.: 748,716

[22] Filed: Dec. 9, 1976

[51] Int. Cl.² .................................................. C07D 319/08
[52] U.S. Cl. .................................... 260/340.3; 424/278
[58] Field of Search ........................................ 260/340.3

[56] References Cited

U.S. PATENT DOCUMENTS 3,183,157  5/1965  Bhuyan et al. ........................ 424/120

3,501,569  3/1970  Wiley et al. ........................... 424/119

OTHER PUBLICATIONS

Wiley et al., Chem. Abs., 69:59530a.

*Primary Examiner*—Ethel G. Love
*Attorney, Agent, or Firm*—Roman Saliwanchik

[57] ABSTRACT

Novel antibiotics, 7-O-alkylnogarols, prepared by acidic alcoholysis of nogamycin, which are active against various microorganisms, for example, *Bacillus subtilis* and *Lactobacillus casei*. Thus, they can be used to inhibit the growth of the above microorganisms in various environments.

5 Claims, No Drawings

ANTIBIOTICS 7-O-ALKYLNOGAROLS

The invention described herein was made in the course of, or under Contract NO1-CM-43753 with the National Cancer Institute, National Institutes of Health, Bethesda, Md. 20014.

BACKGROUND OF THE INVENTION

The known antibiotic nogalamycin, and a process for its preparation, are described in U.S. Pat. No. 3,183,157. The structure of nogalamycin can be shown as follows:

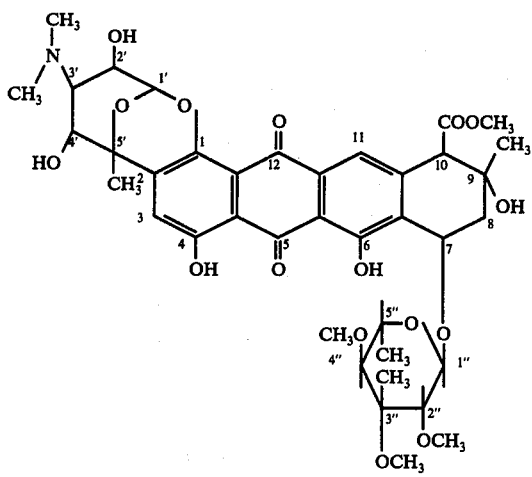

Antibiotics nogalarol and nogalarene, produced by acid hydrolysis of nogalamycin, and o-methylnogalarol, produced by acidic methanolysis of nogalamycin or nogalarol, are disclosed in U.S. Pat. No. 3,501,569.

Nogalamycinic acid is prepared by chemical modification of nogalamycin. The structure of nogalamycinic acid is as follows:

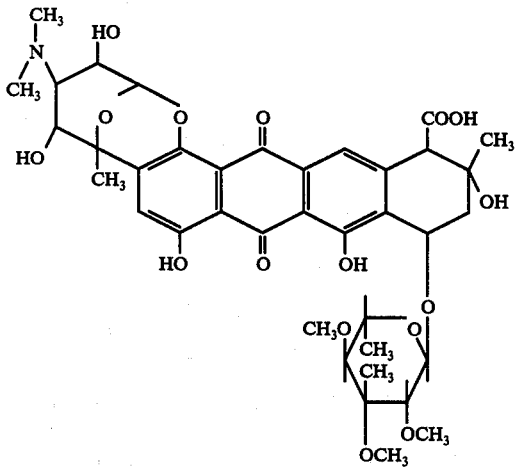

Nogalamycinic acid can be converted to nogamycin by contacting it with dimethylformamide. Nogamycin has the following structural formula:

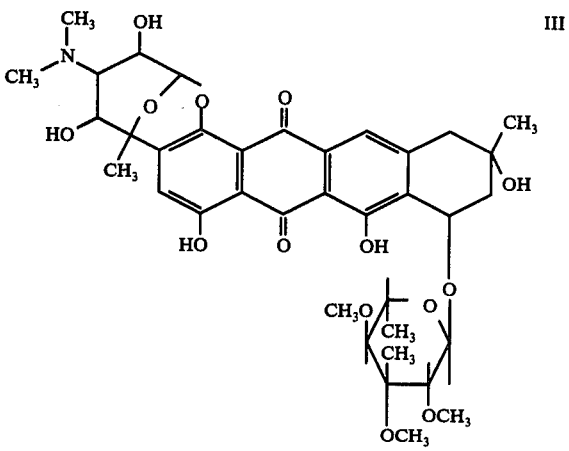

BRIEF SUMMARY OF THE INVENTION

7-O-Alkylnogarols can be prepared by acidic alcoholysis of nogamycin. For example, upon reacting nogamycin with methanolic hydrogen chloride at a temperature of about 50° C. to reflux, there is obtained 7-O-methylnogarol (U-52,047). 7-O-alkylnogarol is biologically active and can be used in various environments to inhibit the growth of susceptible microorganisms. For example, 7-O-alkylnogarol can be used for treating breeding places of silkworms, to prevent or minimize infections which are well known to be caused by *Bacillus subtilis*. Further, 7-O-alkylnogarol can be used to minimize or prevent odor in fish and fish crates caused by contamination with *B. subtilis*.

DETAILED DESCRIPTION OF THE INVENTION

The 7-O-alkylnogarols of the subject invention can be shown by the following structure:

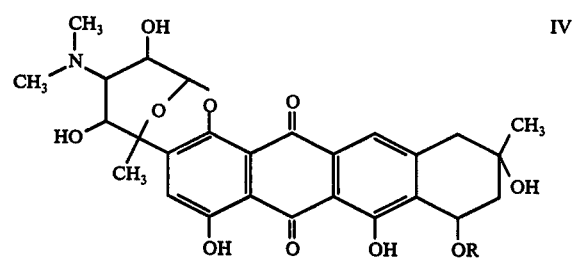

wherein R is an alkyl group of from 1 to 4 carbon atoms, inclusive, and isomeric forms thereof.

7-O-Alkylnogarol can be prepared by acidic alcoholysis of nogamycin. The reaction can be conducted with a mineral acid ranging from about 0.05 N to about 1 N. Examples of acids which can be used are hydrogen chloride, hydrogen bromide, hydrogen iodide, sulfuric acid, phosphoric acid, and the like.

The reaction can be conducted at a temperature of about 50° C. to reflux. Reflux is preferred as lower temperatures prolong the completion of the reaction.

Suitable alcohols which can be used in the reaction are methanol, ethanol, propanol, isopropanol, n-butanol, and isobutanol.

The desired product of the reaction can be recovered from the reaction by extraction with a suitable solvent, for example, methylene chloride (preferred), chloroform and ethyl acetate. The desired product can be recovered from the extract by chromatography on silica gel using suitable solvent systems, for example, $CHCl_3$—MeOH (95:5) and $CHCl_3$—MeOH—$H_2O$ (78:20:2).

7-O-Alkylnogarol can be acylated under standard acylating conditions with an appropriate acid halide or anhydride to give the acylated compound. The acylation is carried out in the presence of an acid-binding agent. Suitable acid-binding agents include: amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, tertbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, amino-, cyano-, and lower alkoxy- hydrocarbon carboxylic acids include hydrocarboncarboxylic acids as given above which are substituted by one or more of halogen, nitro, amino, cyano, or lower alkoxy, advantageously lower alkoxy of not more than six carbon atoms, for example, methoxy, ethoxy, propoxy, butoxy, amyloxy, hexyloxy groups and isomeric forms thereof. Examples of such substituted hydrocarbon carboxylic acids are:

mono-, di- and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
cyanopropionic acid;
ethoxyformic acid (ethyl hydrogen carbonate);
and the like.

The acylated compound, as described above, can be used in animals for the same biological purposes as disclosed above for 7-O-alkylnogarol. For example, the acylated compound can be given in oral form to an animal possessing the necessary enzyme to remove the acyl group, thus freeing the parent antibiotic compound which then inhibits susceptible bacteria.

Acid addition salts of the invention compounds can be made by neutralizing the compound with an appropriate acid to below about pH 7.0, and advantageously to about pH 2 to pH 6. Suitable acids for this purpose include tartaric, glucuronic, and lactic which give water soluble salts, and hydrochloric, sulfuric, phosphoric, sulfamic, hydrobromic, and the like which give relatively water insoluble salts. Acid salts of 7-alkylnogarol can be used for the same biological purposes as the parent compound.

7-O-Methylnogarol has demonstrated antitumor activity against L1210 in vitro and in vivo, and against P388 in vivo. Both in vivo tests results were in mice.

The following examples are illustrative of the process and products of the invention, but are not to be construed as limiting. All percentages are by weight and all solvent mixture proportions are by volume unless otherwise noted.

PREPARATION OF NOGAMYCIN

A solution of 12.3 g of nogalamycinic acid in a mixture of 20 ml of DMF and 50 ml of $CH_3OH$ was prepared by heating. After the solution had stood at room temperature overnight, it was put on 500 g of silica and eluted with $CHCl_3$—MeOH starting with 99:1 and gradually increasing the concentration of $CH_3OH$ until a ratio of 4:1 was reached. The elution was followed by thin layer chromatography (tlc) ($CHCl_3$—MeOH—$H_2O$; 78:20:2) and collecting those fractions containing only nogamycin (Rf 0.5). A total of 3.9 g was obtained. One and one-half grams was recrystallized from acetone-$CH_3OH$ (85:15). Obtained: 259 mg, mp 210°–215° C.; $\alpha_D + 273°$ (C 0.923, $CHCl_3$); uv (EtOH) λmax nm 236 (ε 51,700), 259 (ε 25,850), 290 (ε 10,050) and 478 (ε 16,100); ir (Nujol) 3500, 1670, 1630, 1575, 1295, 1230, 1110, 1055, 1005, 920, 890, 838, 778, 762 and 724 cm$^1$; mass spectrum m/e 729; $^1H$ NMR ($d_7$—DMF) 1.14, 1.23, 1.37, 1.69 (12 H, 4 $CH_3C$), δ 2.07–2.38, 2.83–3.0 (m, 4 H, 2 $CH_2$), 2.42 [s, 6 H, $(CH_3)_2N$], δ 3.13, 3.42, 3.52 (3 S, 9 H, 3 $CH_3O$), 3.3–4.2 (m, CHO, CHN), 4.95 (m, 1 H, benzylic CHO), δ 5.32 (d, 1 H, anomeric), δ 5.68 (1 H, anomeric) δ 7.16, 7.32 (2s, 2 H, aromatic); $^{13}C$ NMR ($CDCl_3$) δ 15.2, 18.3, 24.2, 30.4 (4 $CH_3C$), 30.8 ($CH_2$), δ 41.5 [$(CH_3)_2N$], δ 44.1 ($CH_2$) δ 48.7, 59.0, 61.4 (3 $CH_3O$), δ 66.4–88.6 (CO and CN), δ 96.79 and 99.81 (anomeric), δ 113.1–161.4 (aromatic), δ 179.7 and 190.8 (carbonyl).

Anal. calcd. for $C_{37}H_{47}NO_{14}$: C, 60.96; H, 6.55; N, 1.92. Found: C, 58.55; H, 6.42; N, 1.94.

EXAMPLE 1

7-O-Methylnogarol

A solution of 5 g (6.8 mmoles) of nogamycin in 200 ml of 0.26 N methanolic hydrogen chloride was heated under reflux for 2 hours. The cooled solution was evaporated under reduced pressure to about 75 ml. The solution was diluted with 250 ml of $H_2O$ and extracted with three 50-ml portions of $CHCl_3$. The aqueous layer was then adjusted to pH 7.2 with 50% NaOH solution and extracted with three 100-ml portions of $CHCl_3$. The combined $CHCl_3$ extracts were evaporated to dryness under reduced pressure. The residue (about 4 g) was chromatographed on 125 g of silica gel eluting with $CHCl_3$—MeOH (95:5) and collecting two hundred and sixty-six 10-ml fractions. Fractions 87–185 were combined on the basis of a color peak and thin layer chromatography (tlc) in $CHCl_3$—MeOH—$H_2O$ (78:20:2). Evaporation under reduced pressure gave 1.97 g (53%), mp 248°–253° C.; Rf (above system) 0.64; $\alpha_D + 958°$ (c 0.163, $CHCl_3$); uv (EtOH) $\lambda$max 235 nm ($\epsilon$ 41,200), 251 nm ($\epsilon$ 25,500), 257 nm ($\epsilon$ 24,150), 290 nm ($\epsilon$ 10,500), 479 nm ($\epsilon$ 15,530); ir (Nujol) 3470, 1675, 1625, 1580, 1470, 1430, 1405, 1385, 1300, 1230, 1135, 1115, 1085, 1065, 1015, 950, 925, 890, 870, 850, and 790 $cm^{-1}$; mass spectrum m/e 541; $^1$H NMR ($CDCl_3$—$CD_3OD$) $\delta$ 1.45, 1.73 (2s, 6 H, 2 $CH_3C$), $\delta$ 2.32–2.50, 2.72–3.1 (m, 4 H, 2 $CH_2$), $\delta$ 2.58 (s, 6 H, $(CH_3)_2N$), $\delta$ 3.60 (s, 3 H, $CH_3O$), $\delta$ 3.3–4.2 (m, CHO and CHN), $\delta$ 4.83 (m, 1 H, benzylic H), $\delta$ 5.82 (d, 1 H, anomeric), $\delta$ 6.77, 7.25 (2s, 2 H, aromatic); $^{13}$C NMR ($CDCl_3$—$CD_3OD$) $\delta$ 23.9, 30.0 (2 $CH_3C$), $\delta$ 36.1 ($CH_2$), $\delta$ 41.6 [$(CH_3)_2N$], $\delta$ 44.1 ($CH_2$), $\delta$ 57.9 ($CH_3O$), $\delta$ 66.1, 68.3, 70.5, 71.4, 72.8, 75.2 (CO and CN), $\delta$ 97.6 (anomeric), $\delta$ 112.6, 114.5, 116.2, 120.5, 125.6, 129.3, 133.0, 137.7, 146.2, 148.2, 155.6, 161.1 (aromatic), $\delta$ 179.7, 190.9 (quinone carbonyl). Anal. Calcd. for $C_{28}H_{31}NO_{10}$: C, 62.10; H, 5.78; N, 2.59. Found: C, 62.21; H, 5.94; N, 2.66.

| Antimicrobial Activity of 7-0-Methylnogarol hz,1/32 | | |
|---|---|---|
| Organism | 7-0-Methylnogarol | Tartrate |
| Bacillus subtilis | 20 mm | 32 mm |
| Lactobacillus casei | 26 mm | 32 mm |

The above antimicrobial tests were run by dipping 13 mm filter paper discs into a 1 mg/ml solution of the test substance in methanol (uptake about 20 microliters/disc) and placing the discs on agar plates containing a 1.3 mm layer of agar freshly seeded with the test organism. Discs dipped in methanol alone gave no inhibition zones. The agar media used, available from the Difco Company, Detroit, Mich., were as follows: for B. subtilis, Streptomycin agar; and for L. casei, thioglycollate agar. The plates were incubated 18 to 24 hours at 37° C. before reading the zones.

EXAMPLE 2

Tartrate Salt Solution

7-O-Methylnogarol is dissolved in a 2 N tartaric acid solution containing two moles of tartaric acid per mole of 7-O-methylnogarol to give a 7-O-methylnogarol tartrate salt solution.

By substituting other 7-O-alkylnogarol, as defined herein, for 7-O-methylnogarol, there is obtained the corresponding 7-O-alkylnogarol tartrate salt solution.

EXAMPLE 3

By substituting the following alcohols in Example 1 for methanol, there is obtained the corresponding 7-O-alkylnogarols: ethanol, propanol, isopropanol, n-butanol, and isobutanol.

We claim:

1. 7-O-Alkylnogarol, a compound having the following structure:

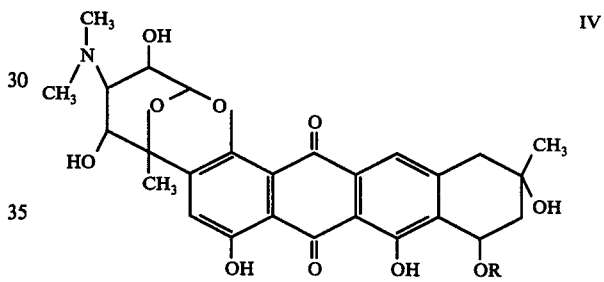

wherein R is alkyl of from 1 to 4 carbon atoms, inclusive, and isomeric forms thereof.

2. Biologically acceptable acid addition salts of the compound of claim 1.

3. 7-O-Methylnogarol, a compound according to claim 1, wherein R is methyl.

4. 7-O-Methylnogarol tartrate.

5. Acylates of 7-O-alkylnogarol wherein said acyl group consists of hydrocarbon carboxylic acid acyl of from 2 to 18 carbon atoms, inclusive: halo-, nitro-, amino-, cyano-, and lower alkoxy-substituted hydrocarbon carboxylic acid acyl of from 2 to 18 carbon atoms, inclusive.

* * * * *